(12) United States Patent
Birikh et al.

(10) Patent No.: US 10,793,886 B2
(45) Date of Patent: *Oct. 6, 2020

(54) METHOD FOR CONVERTING XYLOSE INTO XYLULOSE

(71) Applicant: METGEN OY, Kaarina (FI)

(72) Inventors: Klara Birikh, Kaarina (FI); Anu Minna Maaret Suonpää, Kaarina (FI); Matti Wilhelm Heikkilä, Kaarina (FI)

(73) Assignee: METGEN OY, Kaarina (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/311,612

(22) PCT Filed: Jun. 20, 2017

(86) PCT No.: PCT/EP2017/065044
§ 371 (c)(1),
(2) Date: Dec. 19, 2018

(87) PCT Pub. No.: WO2017/220550
PCT Pub. Date: Dec. 28, 2017

(65) Prior Publication Data
US 2019/0185892 A1   Jun. 20, 2019

(30) Foreign Application Priority Data
Jun. 20, 2016   (EP) .................................... 16175236

(51) Int. Cl.
*C12P 19/02*   (2006.01)
*C12P 19/24*   (2006.01)

(52) U.S. Cl.
CPC ............... *C12P 19/02* (2013.01); *C12P 19/24* (2013.01); *C12Y 503/01005* (2013.01); *C12P 2201/00* (2013.01)

(58) Field of Classification Search
None
See application file for complete search history.

(56) References Cited

U.S. PATENT DOCUMENTS

2013/0143277 A1*   6/2013   Gutierrez ................ C12N 1/22
435/99

FOREIGN PATENT DOCUMENTS

WO   2012173659 A2   12/2012

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession B5YAD2. Nov. 25, 2008 (Year: 2008).*
Accession B8E394. Mar. 3, 2009 (Year: 2009).*
Anonymous, "UNIPROT: B5YAD2", Nov. 25, 2008 (Nov. 25, 2008), XP055312140, Retrieved from the Internet: URL: http://this.internal.epo.org/exam/dbfetch.jsp?id=UNIPROT:B5YAD2, retrieved on Oct. 19, 2016; sequence.
Anonymous, "UNIPROT: B8E394", Mar. 3, 2009 (Mar. 3, 2009), XP055312190, Retrieved from the Internet: http://bis.internal.epo.org/exam/dbfetch.jsp?id=UNIPROT:B8E394, retrieved on Oct. 19, 2016; sequence.
Bhosale, Snehalata H. et al., "Molecular and Industrial Aspects of Glucose Isomerase Functional Role of Esssential Amino Acid Residues", Microbiological Reviews, vol. 60(2), Jun. 1, 1996 (Jun. 1, 1996), pp. 280-300, XP055311888, Retrieved from the Internet: https://www.ncbi.nlm.nih.gov/pmc/articles/PMC239444/pdf/600280.pdf, [retrieved on Oct. 18, 2016], p. 285, col. 2, paragraph 3.
Dobson, " Xylose Isomerase Protein, SEQ ID 164", XP002763546, Database accession No. BAJ38408, Dec. 20, 2012 (Dec. 20, 2012).
Mathrani Indra Madan et al., "Thermophilic and Alkalophilic Xylanases from Several Dictyoglomus Isolates", Applied Microbiology and Biotechnology, vol. 38, No. I, 1992, pp. 23-27, XP002763547, ISSN: 0175-7598.
PCT International Search Report and Written Opinion, Application No. PCT/EP2017/065044, dated Sep. 29, 2017, 12 pages.

* cited by examiner

*Primary Examiner* — Christian L Fronda
(74) *Attorney, Agent, or Firm* — Patent Law Works, LLP

(57) ABSTRACT

The invention is in the field of enzymology. More in particular, it provides a method for the isomerization of xylose into xylulose wherein the xylose is derived from lignocellulosic material. More in particular, it provides a method for converting xylose into xylulose comprising the steps of: providing a composition comprising water, xylose and lignin, enzymatically converting the xylose to xylulose in the presence of a xylose isomerase, and optionally purifying the xylulose from the solution, wherein the xylose isomerase comprises an amino acid sequence that is at least 90% identical with the sequence according to SEQ ID NO: 1 or SEQ ID NO: 2

Figure 1:
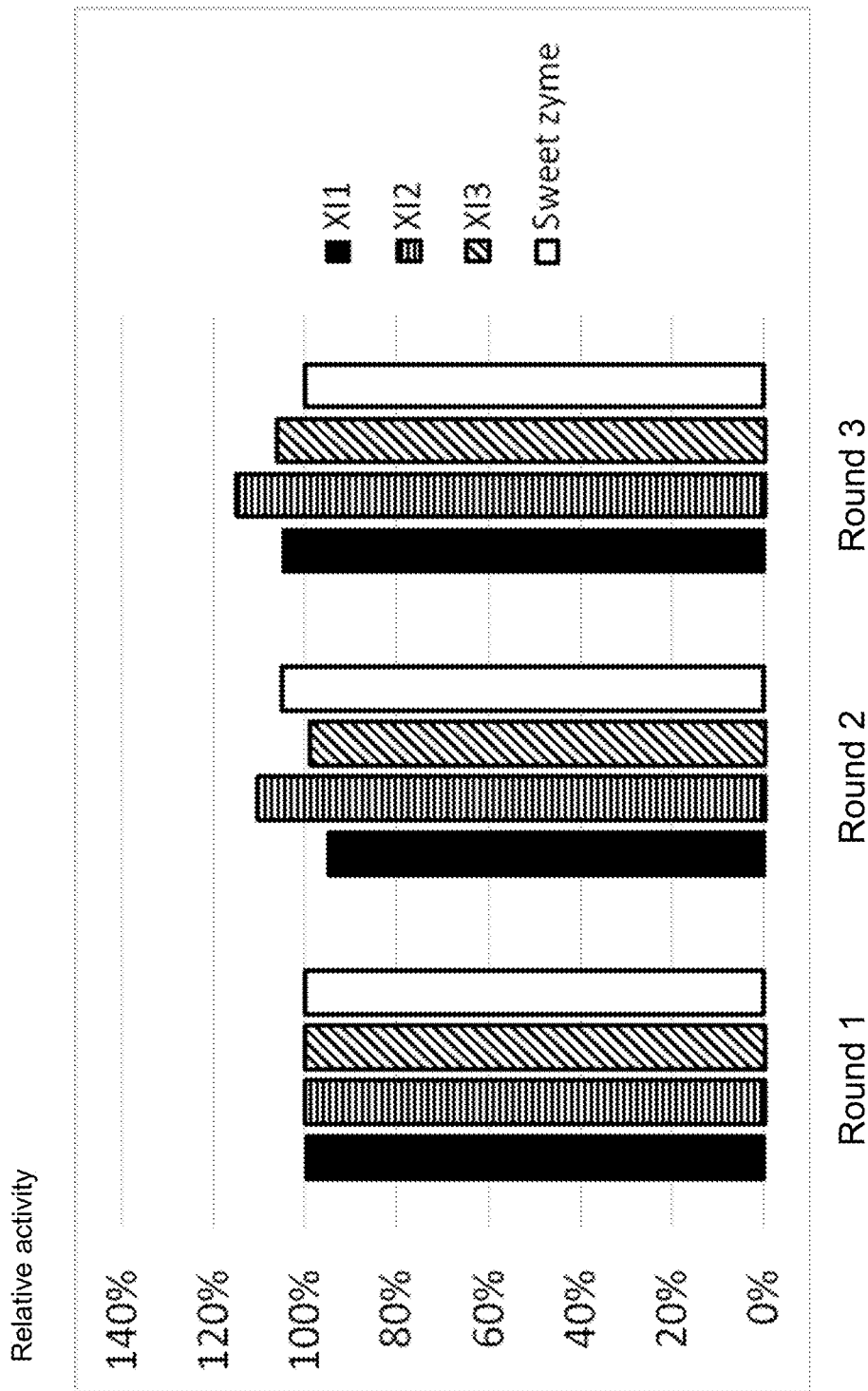

17 Claims, 3 Drawing Sheets
Specification includes a Sequence Listing.

Relative residual activity [%]

SEQUENCE LISTING

<160> NUMBER OF SEQ ID NOS: 7

<210> SEQ ID NO 1
<211> LENGTH: 368
<212> TYPE: PRT
<213> ORGANISM: Dictyoglomus thermophilum

<400> SEQUENCE: 1

```
Met Pro Phe Val Asp His Arg Ala Gln Lys Ile Arg Arg Ser Lys Glu
 1               5                  10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Val
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Glu Cys Tyr Phe Asp Pro
            340                 345                 350

Glu Asn His Arg Gly Glu Leu Glu Leu Ile Leu Ala Gly Asn His Lys
        355                 360                 365
```

<210> SEQ ID NO 2
<211> LENGTH: 368
<212> TYPE: PRT
<213> ORGANISM: Dictyoglomus turgidum

<400> SEQUENCE: 2

```
Met Pro Phe Val Asp His Arg Asn Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Gly Ile Pro Glu Arg Ile Glu Met Ala Ala Glu
    50                  55                  60

Met Ala Lys Tyr Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Thr
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Ile
        115                 120                 125

Ala Tyr Glu Arg Leu Val Asn Gly Leu Lys Leu Val Lys Glu Ala Asn
130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
        355                 360                 365
```

<210> SEQ ID NO 3

```
<211> LENGTH: 444
<212> TYPE: PRT
<213> ORGANISM: Thermotoga Neapolitana

<400> SEQUENCE: 3

Met Ala Glu Phe Phe Pro Glu Ile Pro Lys Val Gln Phe Gly Lys
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
                35                  40                  45

Trp His Thr Phe Val Asn Glu Gly Arg Asp Pro Phe Gly Asp Pro Thr
        50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
370                 375                 380

Glu Lys Tyr Arg Ser Phe Arg Glu Gly Ile Gly Arg Asp Ile Val Glu
```

```
                385               390               395               400
            Gly Lys Val Asp Phe Glu Lys Leu Glu Glu Tyr Ile Ile Asp Lys Glu
                            405                 410                 415

Thr Ile Glu Leu Pro Ser Gly Lys Gln Glu Tyr Leu Glu Ser Leu Ile
                            420                 425                 430

Asn Ser Tyr Ile Val Lys Thr Ile Leu Glu Leu Arg
                            435                 440

<210> SEQ ID NO 4
<211> LENGTH: 1107
<212> TYPE: DNA
<213> ORGANISM: Dictyoglomus thermophilum

<400> SEQUENCE: 4
atgccgtttg ttgatcatcg tgcacagaaa attcgtcgca gcaaagaaga actgctgaaa        60
catatgcaga ccttcaaact ggatctgaaa tttagcgtgg gcatctggta ttttacaccg       120
ggtggtggtc gttttcatga accgtatgtt gaacagaaaa gcattccgga acgtattgaa       180
atggcagcag aaatggcaaa atttggcgtg aaaggtattg aagcacatta tccggctgaa       240
gtgaatgaag aaaatctgca cctgtataaa cagctggaaa agaagcagg tattcgtctg        300 gttgcagttc cgctgagcct gttttatgat aaaatctttg aatttggcag cctgagcaac       360
ccgtatgaaa aatatcgtaa agttgcctat gaacgcctgg tgaatggtct gaaactggtt       420
aaagaagcaa acgccgatat ttgcattatt ggcctggta ttgatggcta tacctatagc        480
tatggtcacc tgtattatca catgtgggat acctttgaag aactggttgc acaggcaatg       540
gatgaagttc gggtgttca ggttgcaatt gaaccgaaac cgtatgaacc ggcaccgaat        600
aacatttatc gtaccaccgc agatggtatt ctggcagcac gtgatattga agcgcgtctg       660
aaaaatccgg aaacctgaa actgctgcaa gaaggtcacg cactggttgg tctgaatccg        720
gaagttggtc atgttcgtat ggttttgaa gatctgccgt atgcatatgc ccgtgttgca        780
cgtgaaggtc gtctgtttca tacccattgg aatagccagc cgctgggtaa ttatgatcag       840
gatctgaata ttggtgtggt ggattgggat agcaccgaag cactgctgta ccctgaaa        900 atggttggtt atcagggcta ttttggcatc gatatcaatc cggaacgcat gccggttatt       960
aaagccattg aaattaacac caaagtgctg cagattatga cgaacgcat gaacgtctg        1020 ccgcatgatc gtattattga gtgttatttt gaccctgaga tcatcgtgg tgaactggaa       1080 ctgattctgg ccgaaaatca taaataa                                         1107

<210> SEQ ID NO 5
<211> LENGTH: 1107
<212> TYPE: DNA
<213> ORGANISM: Dictyoglomus turgidum

<400> SEQUENCE: 5
atgccgtttg tggatcatcg taatcagaaa attcgtcgca gcaaagaaga actgctgaaa        60
catatgcaga ccttcaaact ggatctgaaa tttagcgtgg gcatctggta ttttacaccg       120
ggtggtggtc gttttcatga accgtatgtt gaacagaaag gtattccgga acgtattgaa       180
atggcagcag aaatggcaaa atatggcgtt aaaggtatcg aagcacatta tccggctgaa       240
gtgaatgaag aaaatctgca cctgtataaa cagctggaaa agaaaccgg tattcgtctg        300 gttgcagttc cgctgagcct gttttatgat aaaatctttg aatttggcag cctgagcaac       360
ccgtatgaaa aatatcgtaa aattgcctat gaacgcctgg tgaatggtct gaaactggtt       420
```

```
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcacgtctg    660
aaaaatccgg aaaacctgaa actgctgcaa aaggtcacg cactggttgg tctgaatccg     720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta tacccctgaaa   900 atggttggtt atcagggcta ttttggcatc gatattaatc cggaacgcat tccggttgtt    960
aaagccattg aaattaacac caaagtgctg cagattatga cgaacgcat tgaacgtctg    1020 ccgcatgatc gtattattga gtgttatttt gaccctgaga atcatcgtgg tgaactggaa   1080
ctgattctgg ccgaaaatca tcgttaa                                       1107

<210> SEQ ID NO 6
<211> LENGTH: 1335
<212> TYPE: DNA
<213> ORGANISM: Thermotoga Neapolitana

<400> SEQUENCE: 6
atggcagaat ttttcccgga aattccgaaa gttcagtttg aaggtaaaga agcaccaat     60 ccgctggcct ttaaattcta tgatccggaa gaaatcattg acggcaaacc gctgaaagat   120
catctgaaat ttagcgttgc attttggcac accttttgtga atgaaggtcg tgatccgttt   180
ggtgatccga ccgcagatcg tccgtggaat cgttataccg atccgatgga taaagcattt    240
gcacgtgttg atgcactgtt tgaattttgc gaaaaactga acatcgagta tttctgcttt    300
cacgatcgcg atattgcacc ggaaggtaaa accctgcgtg aaaccaacaa aattctggat    360
aaagtggtgg aacgcatcaa agaacgtatg aaagatagca atgttaaact gctgtggggc    420
accgcaaacc tgtttagcca tccgcgttat atgcatggtg cagcaaccac ctgtagcgca    480
gatgtttttg cctatgcagc agcacaggtt aaaaaagcac tggaaatcac caaagaactg    540
ggtggtgaag ttatgttttt tggggtggt cgtgaaggct atgaaacact gctgaatacc    600
gatctgggtt ttgaactgga aaatctggca cgttttctgc gtatggcagt tgattatgca    660
aaacgcattg gttttaccgg tcagtttctg attgaaccga aaccgaaaga ccgaccaaa     720 caccagtatg attttgatgt tgcaaccgcc tatgcctttc tgaaaagtca tggtctggat    780
gagtacttca atttaacat cgaagcaaat catgcaaccc tggcaggtca taccttcag     840 catgaactgc gcatggcacg cattctgggt aaactgggta gcattgatgc aaatcagggt    900
gatctgctgc tgggttggga tacagatcag tttccgacca atgttatgaa taccacctg    960 gcaatgtatg aagttattaa agcaggcggt tttaccaaag tggcctgaa ttttgatgcc   1020 aaagttcgtc gtgcaagcta aaagttgag gacctgttta ttggtcatat cgcaggtatg   1080
gatacctttg cactgggttt taaagttgcc tacaaactgg ttaaagatgg cgtgctggat   1140
aaattcatcg aagaaaaata tcgcagcttt cgcgaaggta ttggtcgtga tattgttgaa   1200
ggcaaagtgg attttgagaa actggaagag tacatcatcg ataaagaaac cattgaactg   1260
```
ccgagcggca aacaagaata tctggaaagc ctgattaaca gctacatcgt gaaaaccatt 1320
ctggaactgc gttaa 1335

<210> SEQ ID NO 7
<211> LENGTH: 388
<212> TYPE: PRT
<213> ORGANISM: Streptomyces murinus

<400> SEQUENCE: 7

```
Met Ser Phe Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Thr Val Gln Arg Leu Ala Glu Leu Gly Ala
        35                  40                  45

Tyr Gly Val Thr Phe His Asp Asp Leu Ile Pro Phe Gly Ser Ser
    50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Gly Asn Ile Asp Leu Ala Ala Glu
        115                 120                 125

Leu Gly Ala Lys Thr Tyr Val Ala Trp Gly Gly Arg Glu Gly Ala Glu
    130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ala Gln Gly Tyr Asp Leu
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Thr Ala Gly Tyr Glu Gly Pro Arg His Phe Asp Phe
        275                 280                 285

Lys Pro Pro Arg Thr Glu Asp Phe Asp Gly Val Trp Ala Ser Ala Ala
    290                 295                 300

Gly Cys Met Arg Asn Tyr Leu Ile Leu Lys Asp Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Gln Pro Thr Ala Ala Asp Gly Leu Asp Ala Leu Leu Ala
```

-continued

```
                    340                 345                 350
Asp Arg Ala Ala Phe Glu Asp Phe Asp Val Asp Ala Ala Ala Ala Arg
            355                 360                 365

Gly Met Ala Phe Glu His Leu Asp Gln Leu Ala Met Asp His Leu Leu
    370                 375                 380

Gly Ala Arg Gly
385
```

METHOD FOR CONVERTING XYLOSE INTO XYLULOSE

FIELD OF THE INVENTION

The invention is in the field of enzymology. More in particular, it provides a method for the isomerization of xylose into xylulose wherein the xylose is derived from lignocellulosic material.

BACKGROUND OF THE INVENTION

Xylulose is a ketopentose, a monosaccharide containing five carbon atoms, and including a ketone functional group. It has the chemical formula $C_5H_{10}O_5$. In nature, it occurs in both the L- and D-enantiomers.

Xylulose is an important intermediate in the alcoholic fermentation of xylose by yeasts. Because of the potential economic significance of this process, much attention has been paid to the mechanism and regulation of xylose fermentation.

A number of methods have been described for the production of xylulose. Chemical methods generally give low yields, and the formation of isomers is difficult to avoid.

Xylose isomerase is an enzyme which converts xylose into xylulose in a reversible reaction with an equilibrium around 1:1 ratio of xylose and xylulose. The enzyme may be obtained from many different species of bacteria such as *Streptomyces, Actinoplanes, Microbacterium* and *Bacillus*, and the enzyme is or has been marketed by companies such as Enzyme Bio-systems, Genencor, Gist-Brocades, Solvay Enzyme Inc and Novo Nordisk.

Most successful commercial xylose isomerases are immobilized and as a consequence are very stable with an extremely long half life. Commercially these enzymes are mostly used for converting glucose into fructose (an activity which many xylose isomerases display) to obtain so called High Fructose Corn Syrup. In a typical process, the immobilized isomerase is loaded in a column and substrate (feed stock) is passed through at a rate that produces an effluent containing 42% fructose. Prerequisite however, is that the feed stock is a refined hydrolysate containing 93-96% glucose. Efficient refining is required in order to remove impurities that otherwise would cause inactivation of the glucose isomerase.

The emerging field of second generation biofuel and bio-renewable materials such as plastics, utilize lignocellulose biomass as the source of sugars. Lignocellulose therein is preferably obtained from plant dry matter from un-eatable plants or parts of plants, so called lignocellulosic biomass. It is the most abundantly available raw material on earth. It is composed of carbohydrate polymers (cellulose, hemicellulose), and an aromatic polymer (lignin). These carbohydrate polymers contain different sugar monomers (six and five carbon sugars) and they are tightly bound to lignin.

Processing of lignocellulosic biomass includes steps allowing the release of sugars from polymeric forms, such as biomass pretreatment and hydrolysis. This is often followed by microbial fermentation of the aforementioned sugars. As yeast cannot metabolize xylose, but can metabolize xylulose, it is desirable to convert xylose from hydrolyzed plant xylan into xylulose.

An alternative way of valorization of lignocellulosic biomass is converting sugars to chemical building blocks for polymer production. Furfural (IUPAC name: Furan-2-carbaldehyde. $C_5H_4O_2$) is regaining attention as a biobased alternative for the production of a large variety of chemicals, including antacids, fertilizers, plastics and paints. Furfural can be obtained from xylose via isomerization to xylulose. Xylose isomerase may therefore also be employed advantageously in this reaction.

Alternative enzymes for the conversion of lignocellulose derived xylose to xylulose are not yet available but would be highly desirable.

SUMMARY OF THE INVENTION

We found that use of the currently available xylose isomerases in the conversion of lignocellulose-derived xylose into xylulose is hampered by impurities that are present in lignocellulose-derived xylose. These impurities lead to a significant decrease in the stability of the enzyme.

We herein present a xylose isomerase that allows to avoid cumbersome and costly purification steps in the production of xylulose from lignocellulose material The xylose isomerase presented herein is resistant towards some or most, if not all impurities of lignocellulose-derived xylose.

The conversion of xylose derived from a lignocellulose material would greatly benefit from a xylose isomerase enzyme that works in crude hydrolysis mixtures comprising various components of plant material, such as hemicelluloses, cellulose, other sugars and lignin.

We identified a family of xylose isomerases that are particularly suited for the conversion of xylose to xylulose in a process wherein the xylose is derived from a lignocellulose source. Whereas commercial enzymes and other known xylose isomerases are unstable in solutions comprising lignocellulose-derived xylose and require extensive purification of the substrate, two different bacterial xylose isomerases derived from the genus of Diktyoglomus are proven herein to be resistant against the decrease in stability when xylose derived from lignocellulosic material or biomass is used as the substrate. We show herein that lignin inhibits or deactivates or destabilizes the conventional xylose isomerases, whereas bacterial xylose isomerases derived from the genus of Diktyoglomus are resistant against that.

Accordingly, the invention relates to a method for converting xylose into xylulose comprising the steps of:
  a) providing a composition comprising water, xylose and lignin,
  b) enzymatically converting the xylose to xylulose in the presence of a xylose isomerase,
  c) optionally purifying the xylulose from the solution, wherein the xylose isomerase comprises an amino acid sequence that is at least 90% identical with the sequence according to SEQ ID NO: 1 or SEQ ID NO: 2.

LEGEND TO THE FIGURES

FIG. 1: Diagram showing the stability of 4 different xylose isomerases upon 3 consecutive incubations in a pure xylose substrate.

Figure 2:
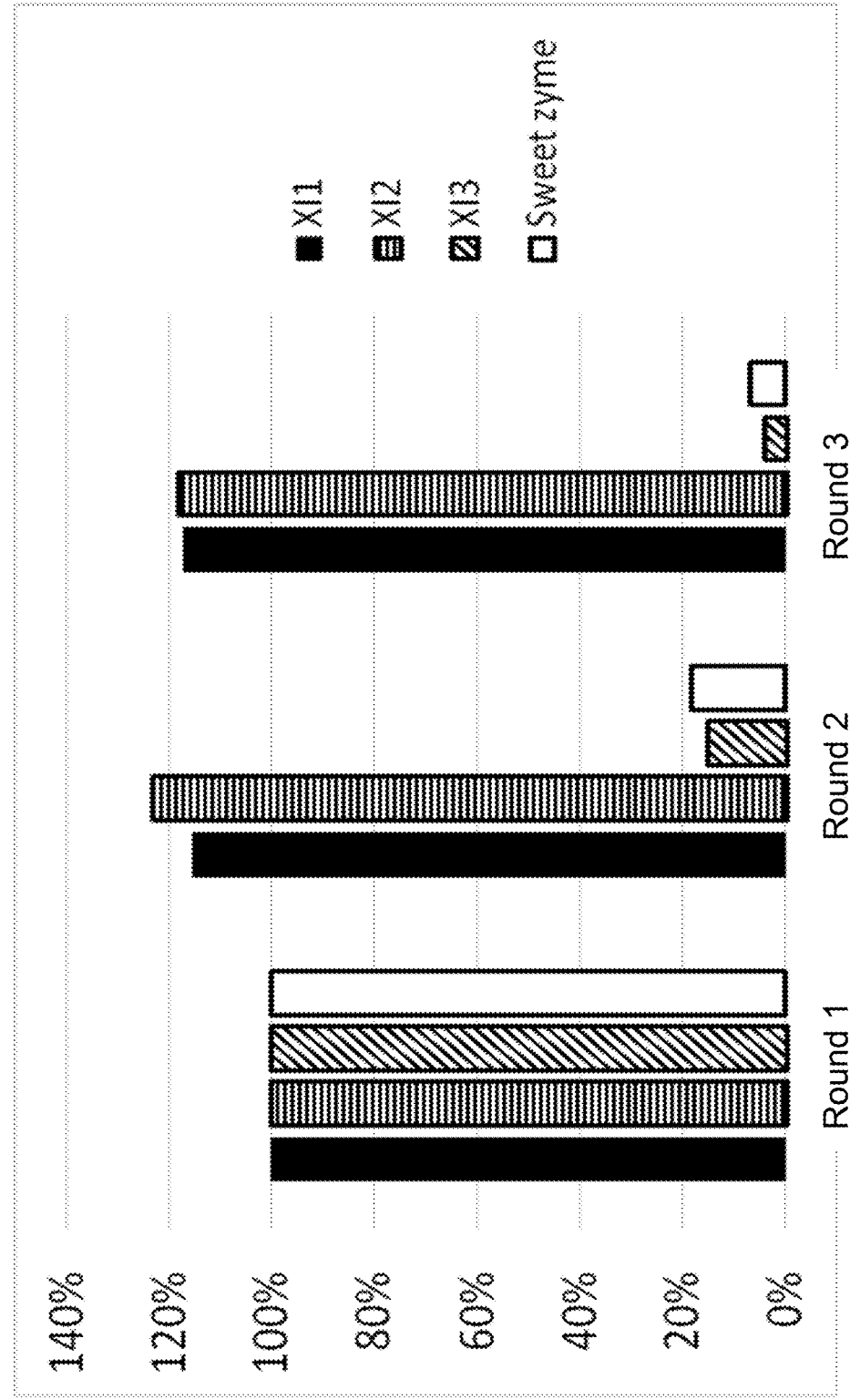

FIG. 2: Diagram showing the stability of 4 different xylose isomerases upon 3 consecutive incubations in a lignocellulose-derived xylose substrate.

Figure 3:
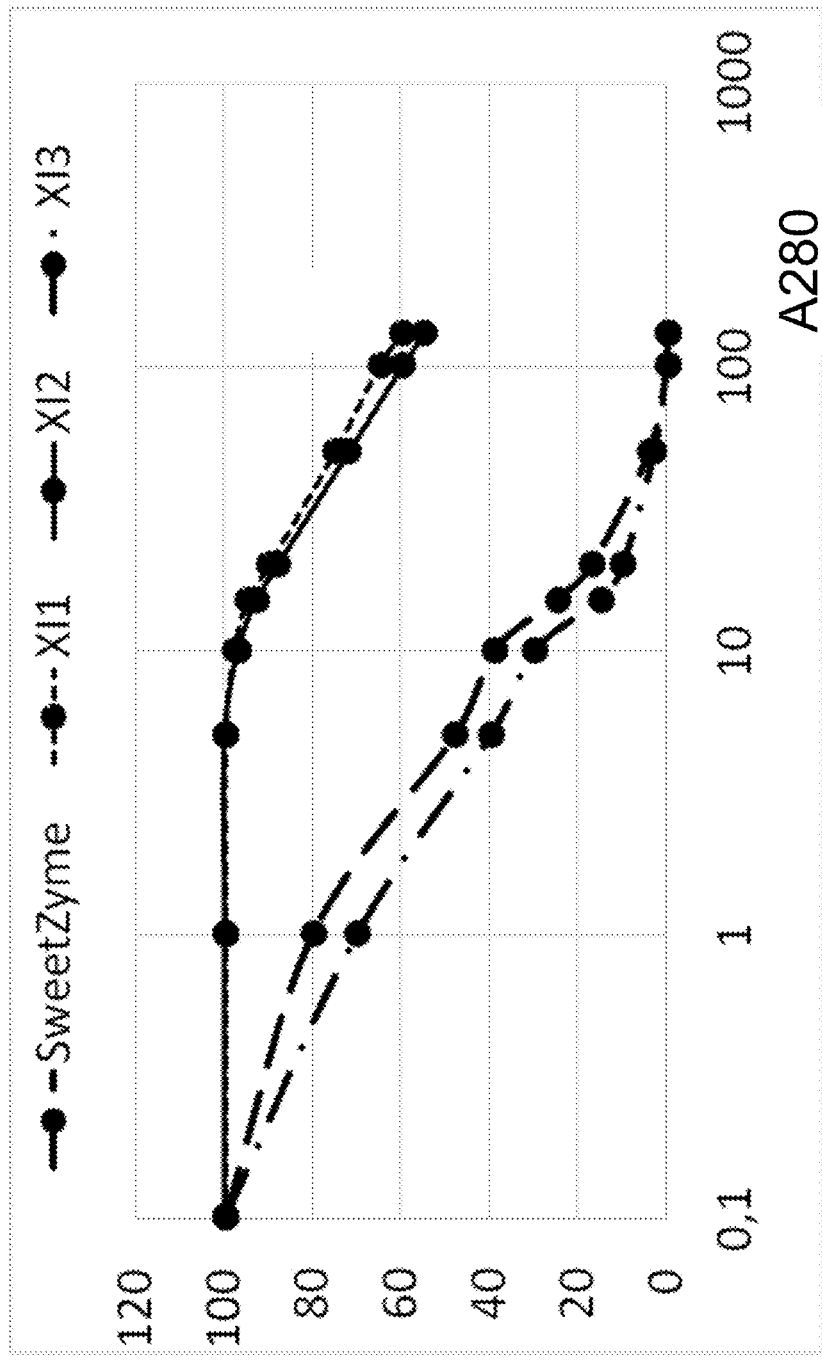

FIG. 3: Graph showing the relative residual activity of 4 different xylose isomerases after 20 hours of incubation with a substrate comprising lignocellulose-derived xylose at 80 degrees Celsius, as a function of lignin content (A280).

DETAILED DESCRIPTION OF THE INVENTION

In enzymology, a xylose isomerase (EC 5.3.1.5) is an enzyme that catalyzes the interconversion of xylose and xylulose. This enzyme belongs to the family of isomerases, specifically those intramolecular oxidoreductases interconverting aldoses and ketoses. The xylose isomerase enzyme has now been observed in nearly a hundred species of bacteria. Xylose-isomerases are also commonly called glucose-isomerases due to their use in the industry to produce fructose from glucose. The systematic name of this enzyme class is D-xylose aldose-ketose-isomerase. Other names in common use include D-xylose isomerase, D-xylose ketoisomerase, and D-xylose ketol-isomerase.

The commercially available xylose isomerase enzymes have been used successfully in the production of high fructose corn syrup (HFCS) but they are not suited for the isomerisation of xylose or glucose obtained from lignocellulose material. Such lignocellulose derived xylose is characterized by the presence of lignin and other sugars derived from hemicellulose and optionally from cellulose.

Lignin is a complex organic material comprising cross-linked phenolic polymers. In spite of its structural diversity, it has a characteristic absorption spectrum in UV range with a peak at 280 nm, which is often used to quantify lignin content. Conveniently, sugars, such as monosaccharides, disaccharides, polysaccharides and hemicelluloses do not have an absorption in UV range.

We developed an assay to determine the inactivation and stability of xylose isomerase (XI) enzymes and found that commercially available XIs were quickly inactivated in a solution containing lignocellulose-derived xylose at isomerization reaction conditions, and that many other XIs from bacterial origin were unstable as well. As a representative example, the results obtained with a XI obtained from *Thermotoga Neapolitana* (SEQ ID NO: 3) and the widely used XI Sweetzyme® from Novozymes are shown herein. The Novozymes XI enzyme is derived from *Streptomyces murinus*; a prototype sequence of a XI from that organism is provided herein as SEQ ID NO: 7.

Surprisingly, we found that two different XIs, derived from *Dictyoglomus thermophilum* and *Dictyoglomus turgidum* (SEQ ID NO: 1 and SEQ ID NO: 2, respectively) were stable in lignocellulose-derived xylose solutions. XI enzymes from *Dictyoglomus* and their homologues are therefore exceptionally suited for the conversion of lignocellulose-derived xylose into xylulose. These XIs are referred herein further as XI1 and XI2.

Xylose isomerases according to SEQ ID NO: 1 and SEQ ID NO: 2 are homologous sequences with a sequence identity of 98%. It may therefore be expected that closely related XIs, such as XIs with an amino acid sequence that is at least 90%, such as 91%, 92%, 93%, 94%, 95%, 96%, or 97% identical with either SEQ ID NO: 1 or SEQ ID NO: 2, will perform in the same way as XI1 and XI2 exemplified herein. Such close homologues may be obtained from natural sources or by directed mutagenesis. The skilled person is well aware of materials and methods for obtaining such close homologues.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq&LINK_LOC=align2seq. Other commercial and open software such as Vector NTI are also suitable for this purpose.

The enzymes that did not retain their stability in lignocellulose-derived xylose substrates (XI3 and Sweetzyme®) had amino acid sequences that were completely unrelated to the sequences provided in SEQ ID NO: 1 and SEQ ID NO: 2. A prototype sequence of a XI from *Streptomyces murinus* (Sweetzyme®) was about 26% identical over 77% of its sequence length whereas the sequence of XI3 can only be aligned with the sequence of XI1 over 44% of the length of the sequences and has 29% identity in that region.

Whereas all enzymes tested were still fully active in a solution comprising pure xylose (FIG. 1, example 4), incubation of the enzymes with lignocellulose-derived xylose, containing approximately 8 gram per liter lignin (A280 of 130), revealed that XI1 and XI2 were superior in that they were not inactivated by the presence of such concentrations of lignin (FIG. 2, example 6). In contrast, it was shown that the commercial enzyme and XI3 retained at most 25% of their activity after 2 hours of incubation at 80 degrees Celsius at pH 8.0 and were almost completely inactive after 3 hours under these conditions (FIG. 2). Repeat experiments with comparable lignin content in the order of 5-10 grams per liter showed the same results.

In an experiment wherein the residual activity of XIs was determined in the presence of varying concentrations of lignin, it was shown that upon incubation of the XIs for 20 hours at 80 degrees Celsius, XI3 and Sweetzyme® were inactivated for more than 20% already at concentrations of lignin corresponding to an A280 of 1.0 (0.06 gram lignin per liter of substrate, FIG. 3, table 1).

At an A280 of 100 (substrate containing 6 gram lignin per liter) the commercial enzyme and XI3 were completely inactivated after 20 hours at 80 degrees Celsius, whereas XI1 and XI2 still retained more than 50% of their activity (FIG. 3, table 1). When commercially available Kraft lignin from hard or soft wood (solubilized in MOPS buffer pH 8.0) was used instead of hydrolysate, similar results were obtained.

Without wanting to be bound by theory, we speculate that lignin, present in the lignocellulose-derived xylose solution causes the loss in stability of the commercial XIs as well as XI3 as tested herein. Lignocellulose-derived xylose also contains other hemicellulose-derived sugars than xylose, but these were found not to inhibit the commercial XI nor XI3 as tested herein.

Hence, the invention relates to a method for the interconversion of xylose and xylulose in the presence of a xylose isomerase, wherein the xylose is derived from lignocellulose-containing biomass, and wherein the xylose isomerase comprises an amino acid sequence that is at least 90% identical with the sequence according to SEQ ID NO: 1 or SEQ ID NO: 2.

The phrase "xylose derived from lignocellulose-containing material" is equivalent to the term "lignocellulose-derived xylose". Both are used herein to indicate that the xylose is contained in a solution comprising a residual amount of lignin, derived from the lignocellulosic material, such as lignocellulose biomass. As such, the term is used to distinguish the xylose from purified xylose, which does not contain lignin.

XI1 and XI2 as disclosed herein and their homologues with at least 90% sequence identity provide advantageous results in comparison to other XIs. In particular in conditions wherein the substrate solution comprises at least 0.06 gram per liter of lignin (A280 of 1.0), such as 0.3 gram lignin per liter (A280 of 5.0) or even 0.6 gram per liter (A280 of 10).

In other terms, the invention relates to a process for converting xylose into xylulose comprising the steps of:
a) providing a composition comprising water, xylose and lignin,
b) enzymatically converting the xylose to xylulose in the presence of a xylose isomerase,
c) optionally purifying the xylulose from the solution, wherein the xylose isomerase comprises an amino acid sequence that is at least 90% identical with the sequence according to SEQ ID NO: 1 or SEQ ID NO: 2.

In a preferred embodiment, the lignin is present in the composition in a concentration of at least 0.06 gram per liter. This corresponds to an absorbance at 280 nm of at least 1.0.

The composition comprising water, xylose and lignin may advantageously be obtained by hydrolyzing a composition comprising lignin, hemicellulose and optionally cellulose. Such hydrolysis is advantageously performed enzymatically, for instance by employing a xylanase.

The composition comprising lignin, hemicellulose and optionally cellulose may advantageously be obtained from lignocellulose-containing material, such as biomass, such as wood, wood pulp or pretreated biomass or pretreated wood. Advantageously, the pretreatment step comprises a steam explosion step and/or an acid pretreatment step.

All these steps are well known in the art and the skilled person is well aware of the metes and bounds of the terms used herein.

EXAMPLES

Example 1: Preparation of a Polypeptide According to SEQ ID NO: 1, 2 or 3

The DNA constructs encoding the polypeptides according to SEQ ID NO: 1, SEQ ID NO: 2 or SEQ ID NO: 3 were designed using codon frequencies optimized for expression in *E. coli* and commercially synthesized and cloned into a plasmid vector based on a standard pET28a+plasmid. The plasmid vector contained a nucleotide sequence encoding peptidyl-prolyl isomerase (PPlase) from Enterobacteriaceae (Protein databank accession number WP_000255997.1). This nucleotide sequence encodes an N-terminal tag to the expressed protein. The recombinant gene was expressed in *Escherichia coli* BL21(DE3) under the control of the T7-RNA-polymerase promoter. This resulted in expression of a protein comprising SEQ ID NO: 1, 2 or 3. Nucleotide sequences encoding the xylose isomerases according to SEQ ID NO: 1, 2 and 3 are provided herein as SEQ ID NO: 4, SEQ ID NO: 5 and SEQ ID NO: 6 respectively.

Example 2: Heterologous Expression of Polypeptides with Xylose Isomerase Activity Protein production was carried out in *E. coli* BL21(DE3) strain according to the plasmid manufacturer protocol available at http://richsingiser.com/4402/Novagen %20pET %20system%20manual.pdf. The incubation temperature for protein production was 30 degrees Celsius, which was found optimal for maximum yield of the active protein. Cells were lysed by suspending the cells in lysis buffer (50 mM Tris-HCl pH7.4, 1% Triton X100, 1 mM CoCl2) and heating at 70 degrees Celsius for 30 min. The xylose isomerase activity was detected in the insoluble fraction only, and could be fully recovered by centrifugation. Thus, thermostable recombinant xylose isomerase was expressed in active insoluble form allowing reuse of the enzyme in several reaction batches.

Example 3: Xylose Isomerase Activity Assay

Xylose isomerase activity (isomerization reaction rate) was determined by measuring xylulose level in the reaction mixture according to the protocol described in Schenk and Bisswanger, A microplate assay for D-xylose/D-glucose isomerase. Enzyme and Microbial Technology (Elsevier Science Inc, N Y, 1998), V22, pp. 721-723.

Measurement was performed in the linear stage of the reaction course wherein product accumulation is linear with time. Ten-microliter aliquots of the reaction mixture were taken and pipette into a 96-well plate, 40 ul of water was added resulting in 50 ul sample. In some cases, higher dilution of the reaction mixture with water was used to prepare 50 ul of the diluted sample to match the dynamic range of the method. 150 ul of a freshly prepared 1:1 mixture (v/v) of solution A (0.05% resorcinol in ethanol) and solution B (0.216 g FeNH4(SO4)2*12 H$_2$O in 1 l concentrated HCl) were added. For color development, the plate was incubated at 80° C. for 40 min. The absorbance was measured with a microplate reader (Thermo) at 630 nM.

Example 4 Xylose Isomerization Activity of Polypeptides Comprising SEQ ID NO: 1, 2 or 3 and Commercial Xylose Isomerase Sweetzyme® in Pure Xylose Solution In this experiment, we compared four xylose isomerases:
(1) recombinant XI1 (SEQ ID NO: 1) produced in *E. coli*,
(2) recombinant XI2 (SEQ ID NO: 2) produced in *E. coli*,
(3) recombinant XI3 (SEQ ID NO: 3) produced in *E. coli*, and
(4)) Xylose isomerase Sweetzyme® (commercial product of Novozymes).

Enzymatic activity was first determined in a xylose solution (130 mM xylose, 10 mM MOPS pH 8.0, 1 mM MgCl2), this is also referred to herein as "pure xylose solution" or "pure xylose substrate".

Sweetzyme® xylose isomerase was dosed 0.1 activity units/mL. Dosages of other xylose isomerases according to SEQ ID NO: 1, 2 or 3 were adapted to achieve the same conversion rate as Sweetzyme® in pure xylose solution under the same conditions (pH=8.0, at 80 degrees Celsius).

The amount of enzyme was selected so that during the reaction time the product formation remains linear. XI1 XI2 and XI3 proteins corresponding to SEQ ID NO: 1-3 respectively, were in the form of suspension of insoluble active aggregates. Sweetzyme® is an immobilized enzyme appearing as small beads.

To test the stability of the enzymes, three consecutive rounds of incubation were performed with pure xylose solution as the substrate. In the first round, after one hour of reaction time, the enzymes showed almost identical activity (FIG. 1). The enzymes were then recovered by centrifugation and after removal of the supernatant, subjected to a second round of incubation with the pure xylose substrate.

For this purpose, fresh pure xylose substrate (130 mM xylose, 10 mM MOPS pH 8.0, 1 mM MgCl2) was added to the pellets containing the enzymes, pellets were re-suspended and reactions were allowed to continue for another hour. After that, enzymes were recovered again and a third round of incubation with pure xylose substrate was carried out the same way. Supernatants from all three reactions with each enzyme were analyzed for xylulose concentration to determine enzyme activity.

FIG. 1 shows the enzyme activities of all four enzyme preparations in the three consecutive rounds.

It can be concluded from this that all four enzyme preparations remain active at 80 degrees Celsius for at least 3 hours without losing any activity, and that all four enzyme preparations can be fully recovered from the mixtures by centrifugation and reused.

Example 5 Preparation of Lignocellulose Hydrolysate

Wood chips, obtained from birch, were submerged in 2% sulfuric acid at a dry matter content of 20% and subjected to a steam explosion pretreatment essentially as described in EP2623607A1. The pretreated material thus contained solubilized fractions of hemicellulose and lignin and insoluble cellulose and part of the lignin. As xylan is contained in the hemicellulose fraction, the liquid fraction was separated from the solids, and solids were washed with water, resulting in 25 g/L xylan and 10 g/L lignin.

This composition was used for producing xylose by enzymatic hydrolysis of xylan. The hydrolysis was carried out using xylanase (from DuPont) under the manufacturer's recommended conditions. The resulting mixture contained 20 g/L xylose (130 mM), 1.8 g/L mannose, approximately 1.7 g/L other sugars and 9 g/L lignin.

Before the isomerization reaction, the pH was adjusted to 8 with sodium hydroxide. The resulting solution is referred to herein further as "hydrolysate" or "hemicellulose hydrolysate" and used for the isomerization reaction.

Example 6 Xylose Isomerization Activity of Polypeptides Comprising SEQ ID NO: 1, 2 or 3 and Commercial Xylose Isomerase Sweetzyme® in Hemicellulose Hydrolysate In this experiment, we compared four xylose isomerases:
(1) recombinant XI1 (SEQ ID NO: 1) produced in *E. coli*,
(2) recombinant XI2 (SEQ ID NO: 2) produced in *E. coli*,
(3) recombinant XI3 (SEQ ID NO: 3) produced in *E. coli*, and
(4)) xylose isomerase Sweetzyme® (commercial product of Novozymes) in an identical set-up as described in Example 4, only this time with the hemicellulose hydrolysate instead of the pure xylose as the substrate.

For this purpose, the substrate was brought to 10 mM MOPS pH 8.0 and 1 mM MgCl2. This substrate solution contained the same xylose concentration as the pure xylose solution used in Example 4. The only difference between the substrate of Example 4 and the substrate described in this Example is that the hemicellulose hydrolysate additionally contained other sugars derived from hemicellulose and lignin.

It was observed that XI1 and XI2 were stable in the hemicellulose substrate for at least three consecutive rounds, whereas XI3 and Sweetzyme® were quickly deteriorating from round to round and eventually became inactive (FIG. 2).

Example 7: Determination of Lignin Content of Substrate

Lignin content of the lignocellulose-derived substrate was determined by measuring the absorbance at 280 nm (A280), wherein an A280 of 1.0 corresponds to a lignin concentration of 0.06 gram per liter.

Example 8: Enzyme Stability as a Function of Lignin Content of Substrate

In this experiment, we compared the stability of four xylose isomerases:
(1) recombinant XI1 (SEQ ID NO: 1) produced in *E. coli*,
(2) recombinant XI2 (SEQ ID NO: 2) produced in *E. coli*,
(3) recombinant XI3 (SEQ ID NO: 3) produced in *E. coli*, and
(4)) xylose isomerase Sweetzyme® (commercial product of Novozymes).

Equivalent amounts of these 4 enzymes were added to a solution comprising 130 mM xylose and varying concentrations of lignin (as measured by absorbance at 280 nm (A280)) and incubated for 20 hours at 80 degrees Celsius.

In detail: hemicellulose hydrolysate with an A280 of 130 was diluted with a solution of 130 mM xylose to obtain substrate solutions with the same amount of xylose (130 mM) and varying concentrations of lignin as measured by absorbance at 280 nm. All substrate solutions were brought to 10 mM MOPS pH 8.0 and 1 mM MgCl2. In that way, identical substrate solutions with a varying lignin content corresponding to an A280 of 0.1 to 130 were obtained. The substrate solutions contained equivalent amounts of xylose isomerase activity as measured using pure xylose as described in example 4.

Incubation was carried out at 80 degrees Celsius for 20 h. Afterwards, the enzyme was recovered and tested for residual activity on pure xylose substrate. Residual activities are shown in table 1 below and in FIG. 3 on a logarithmic scale.

It was found that a substrate containing lignin in an amount corresponding to an A280 of 1.0 (0.06 gram of lignin per liter) already inactivated the commercial enzyme Sweetzyme® and XI3 for more than 20%, whereas the enzymes XI1 and XI2 remained 100% active until a concentration corresponding to an A280 of at least 5 (0.3 gram of lignin per liter). At a lignin content corresponding to an A280 of 100 (6 gram per liter) the commercial enzyme Sweetzyme® and XI3 were completely inactive, whereas XI1 and XI2 retained still at least 60% of their activity.

TABLE 1 relative residual activity of 4 different XIs as a function of substrate lignin content

| A280 | Sweetzyme (R) | XI1 | XI2 | XI3 |
| --- | --- | --- | --- | --- |
| 0.1 | 100 | 100 | 100 | 100 |
| 1 | 80 | 100 | 100 | 70 |
| 5 | 45 | 100 | 100 | 40 |
| 10 | 35 | 98 | 97 | 30 |
| 15 | 25 | 95 | 93 | 18 |
| 20 | 15 | 90 | 88 | 10 |
| 50 | 5 | 75 | 72 | 3 |
| 100 | 0 | 65 | 60 | 0 |
| 130 | 0 | 60 | 55 | 0 |

The invention claimed is:

1. A method of converting xylose into xylulose, the method comprising:
providing a composition comprising water, xylose and at least 0.06 grams per liter lignin, and
enzymatically converting the xylose in the composition to xylulose with a xylose isomerase,
wherein the xylose isomerase comprises an amino acid sequence having at least 95% identity with SEQ ID NO: 1 or SEQ ID NO: 2; and
wherein the xylose isomerase is in fluid contact with the lignin.

2. The method according to claim 1, wherein the composition has an absorbance at 280 nm of at least 1.0.

3. The method according to claim 1, wherein providing the composition comprises providing pretreated lignocellulose-containing material.

4. The method according to claim 3, wherein providing the pretreated lignocellulose-containing material comprises hydrolysis of lignocellulose- containing material.

5. The method according to claim 1, wherein providing the composition comprises removing at least some of the cellulose from cellulose-containing lignocellulose material.

6. The method according to claim 5, wherein removing at least some of the cellulose from the cellulose-containing lignocellulose material comprises treating the cellulose-containing lignocellulose material to release hemicelluloses.

7. The method according to claim 6, wherein treating the cellulose-containing lignocellulose material comprises contacting the cellulose-containing lignocellulose material with acid.

8. The method according to claim 1, further comprising purifying the xylulose from the composition after the conversion of xylose to xylulose.

9. The method according to claim 3, wherein the wherein the lignocellulose-containing material is biomass.

10. The method according to claim 9, wherein the biomass is wood or wood pulp.

11. The method according to claim 10, wherein the wood is soft wood.

12. The method according to claim 4, wherein the hydrolysis is enzymatic hydrolysis.

13. The method according to claim 12, wherein the enzymatic hydrolysis is performed using a xylanase.

14. A method of converting xylose into xylulose, the method comprising:
providing a composition comprising water, xylose and lignin, and
enzymatically converting the xylose in the composition to xylulose with a xylose isomerase,
wherein the xylose isomerase comprises an amino acid sequence having at least 95% identity with SEQ ID NO: 1 or SEQ ID NO: 2;
wherein the xylose isomerase has the same activity in the presence of 0.03 grams per liter lignin as it does in the presence of 0.006 grams per liter lignin.

15. The method according to claim 14, wherein the composition comprises at least 0.03 grams per liter lignin.

16. A method of converting xylose into xylulose, the method comprising:
providing a composition comprising water, xylose and lignin, and
enzymatically converting the xylose in the composition to xylulose with a xylose isomerase,
wherein the xylose isomerase comprises an amino acid sequence having at least 95% identity with SEQ ID NO: 1 or SEQ ID NO: 2;
wherein the xylose isomerase has the same activity in the presence of 0.06 grams per liter lignin as it does in the presence of 0.006 grams per liter lignin.

17. The method according to claim 14, wherein the composition comprises at least 0.06 grams per liter lignin.

* * * * *